(12) United States Patent
Becerra et al.

(10) Patent No.: US 6,984,217 B2
(45) Date of Patent: Jan. 10, 2006

(54) CERVICAL DISTRACTION DEVICE

(75) Inventors: Carlos Becerra, Atlanta, GA (US); Norman A. Smith, Alpharetta, GA (US); Markus Randel, Ballground, GA (US); Tony Copeland, Marietta, GA (US)

(73) Assignee: North American Medical Corporation, Atlanta, GA (US)

( * ) Notice: Subject to any disclaimer, the term of this patent is extended or adjusted under 35 U.S.C. 154(b) by 0 days.

(21) Appl. No.: 10/889,422

(22) Filed: Jul. 12, 2004

(65) Prior Publication Data

US 2005/0010152 A1    Jan. 13, 2005

Related U.S. Application Data

(60) Provisional application No. 60/486,049, filed on Jul. 10, 2003.

(51) Int. Cl.
*A61F 5/00* (2006.01)

(52) U.S. Cl. .......................... 602/33; 602/32
(58) Field of Classification Search ............ 602/32, 602/33; 128/845, 846; 5/621, 622
See application file for complete search history.

(56) References Cited

U.S. PATENT DOCUMENTS

| | | | |
|---|---|---|---|
| 4,583,532 A * | 4/1986 | Jones | 602/32 |
| 5,131,103 A * | 7/1992 | Thomas et al. | 29/25.35 |
| 5,697,894 A * | 12/1997 | Gullichsen et al. | 602/32 |
| 6,171,273 B1 * | 1/2001 | Saunders | 602/38 |

OTHER PUBLICATIONS

Advertisement; Pronex Pneumatic Cervical Traction Device; D.C. Products Review; Jan./Feb. 2004; p. 78.
Advertisement; QUANTUM 400; ChiropracticeBUSINESS, vol. 6, No. 4; Apr. 2004; p. 44.
Brochure; Triton Traction Equipment; Chattanooga Corporation; (Date Unknown); pp. 1-6.
Brochure; Tru-Trac 401 Programmable Memory Traction; 1993 Maxxim Medical; pp. 1-3.
North American Medical Corporation; Manual for Accu-Spina System; 2003; pp. 1-33.
C. Johnson, BA Physics, University of Chicago; Lumbar Support Device; Nov. 2002; pp. 1-2; mb-soft.com.
Pro-Med Products website; Traction Units; 2004; pp. 1-12; www.promedproducts.com.
Catalog; Chattanooga Group Rehabilitation Products; 2003; pp. 1-10.
The Saunders Group Inc. website; Physical Therapy Equipment; 2002; pp. 1-15; www.thesaundersgroup.com.
Spina Systems International, Inc. website; Revolutionary Spina Systems; 2004; pp. 1-4; www.spinaprogram.com.

* cited by examiner

*Primary Examiner*—Henry Bennett
*Assistant Examiner*—Camtu Nguyen
(74) *Attorney, Agent, or Firm*—Patton Boggs, LLP

(57) ABSTRACT

A cervical traction device includes a base, a cervical force application member, and a motor operably attached to the cervical force application member. The motor preferably drives the cervical application member through a direct drive system in order to provide a force to a person's cervical vertebra. The cervical traction device may also include a linear actuator for elevating the person's head to direct the force applied to the cervical vertebra. When integrated on a vertebral distraction machine, the cervical traction device includes its own motor for applying force to the cervical vertebra.

8 Claims, 7 Drawing Sheets

CERVICAL DISTRACTION DEVICE

CROSS-REFERENCE TO RELATED APPLICATIONS

This application claims the benefit of and priority to U.S. Provisional Application No. 60/486,049, filed Jul. 10, 2003, which is hereby incorporated by reference.

BACKGROUND OF THE INVENTION

1. Field of the Invention

The present application relates to cervical traction devices that are used to distract cervical vertebra for relieving pain and discomfort associated with cervical misalignment and compression.

2. Description of Related Art

Vertebral traction machines and vertebral decompression machines (collectively referred to herein as "vertebral distraction machines") have been successfully used to treat vertebral misalignment and compression in people suffering mild to severe back pain. By applying a distractive force to the vertebra, the machines are able to assist in decompressing or realigning the affected vertebra, thereby relieving the associated pain. Although some machines have been developed for home use, most vertebral distraction machines are operated by a skilled therapist or doctor.

Typically, the vertebral distraction machine includes a system for applying the distractive force to a patient lying on a platform or bed of the machine. In most cases, distraction of the vertebra in the back is accomplished by attaching a harness to the waist or legs of the patient. The harness is typically connected to either a flexible rope, cable, or webbing, and a force is applied to pull on the lower body of the patient while the upper body remains stationary. The application of force may be accomplished by hanging weights from the rope, cable, or webbing, but it is more common to apply force using a winch that is turned by a clutch-operated motor. The winch is housed in a pedestal at the foot of the bed on which the patient lies, and the therapist directs the application of force by controlling the clutch-operated motor.

Since it is difficult to isolate the cervical vertebra using lower body harnesses, cervical traction devices have been provided as "add-on" components for vertebral distraction machines. These add-on components typically include a movable head support that is positioned beneath the head of a patient lying on the bed of the distraction machine. The person's head is secured to the movable head support and a force is applied to the head support using ropes, cables, or webbing attached through pulleys to the winch at the pedestal. The primary problem with this method of cervical distraction is that it provides an indirect, flexible power transfer linkage between the motor applying force and the patient's head. This flexible linkage prevents efficient control of the force. Additionally, the forces required for cervical traction are much less than those required for lower vertebral traction; therefore, the conventional motor associated with vertebral distraction machines is oversized and mismatched for applying cervical distraction forces. Some cervical traction devices employ motors positioned nearer to the head of the patient, but these motors are also connected to the patient's head using flexible power transfer equipment such as ropes, cables, and webbing. These devices suffer the same control problems described above.

An additional problem associated with existing cervical traction devices is the unsafe condition that can be created during a power interruption. The clutch-operated motors used with most cervical traction devices completely disengage when power to the motor is interrupted. For a patient undergoing cervical treatment, the rapid relaxation of the cervical distraction force could be painful and cause injury. It would be much preferred to be able to slowly relax the cervical distraction force in the event of a power loss.

A need therefore exists for an improved cervical traction device that eliminates the flexible power transfer equipment associated with existing cervical traction devices. A need further exists for a cervical traction device that does not require use of an outsized and remotely located motor that is used for lower vertebral distraction. Finally, a need exists for a cervical traction device that allows gradual reduction in the cervical distraction force in the event of a power loss or interruption.

BRIEF SUMMARY OF THE INVENTION

A cervical traction device having a base, a cervical force application member, and a motor is provided to apply a force to a cervical vertebra of a person. The cervical force application member is mounted such that it is movable relative to the base, and the motor is operably attached to the cervical force application member by a direct drive system for applying the force to the person's head. The use of a direct drive system eliminates flexibility associated with the power transfer systems of traditional cervical traction devices. The direct drive system greatly improves the amount of control available to the therapist directing the application of the force.

The motor of the cervical traction device is preferably a stepper motor. The stepper motor allows greater incremental control of the cervical distraction forces being applied to the patient. The stepper motor also prevents immediate disengagement of the cervical distraction forces in the event of a power interruption to the motor. When power is interrupted, the stepper motor gradually steps down, which slowly releases the force being applied to the cervical vertebra of the patient.

A cervical traction device according to the present invention may also include driving means for applying a force and direct drive means, coupled to said driving means, for applying the force to a cervical vertebra of a person's neck. Additionally, signal means may be electrically connected to said driving means for signaling said driving means to apply the force. Feedback means may be coupled to said driving means for monitoring the application of force, and safety disengagement means may be coupled to said driving means for stopping said application of force.

A vertebral distraction apparatus according to the present invention may include a bed, a first motor for applying a lower vertebral distraction force to a person, a cervical force application member, and a second motor for applying a cervical distraction force to the cervical force application member. The second motor may be a stepper motor connected by a direct drive system to the cervical force application member. A strain gauge may be connected to the second motor for monitoring the cervical distraction force.

A method for distracting a cervical vertebra according to the present invention includes the steps of providing a support member to support a person's head and communicating a signal to the support member to apply a force to the person's head.

The above as well as additional objectives, features, and advantages of the present invention will become apparent in the following detailed written description.

DETAILED DESCRIPTION OF THE PREFERRED EMBODIMENT

Figure 1:
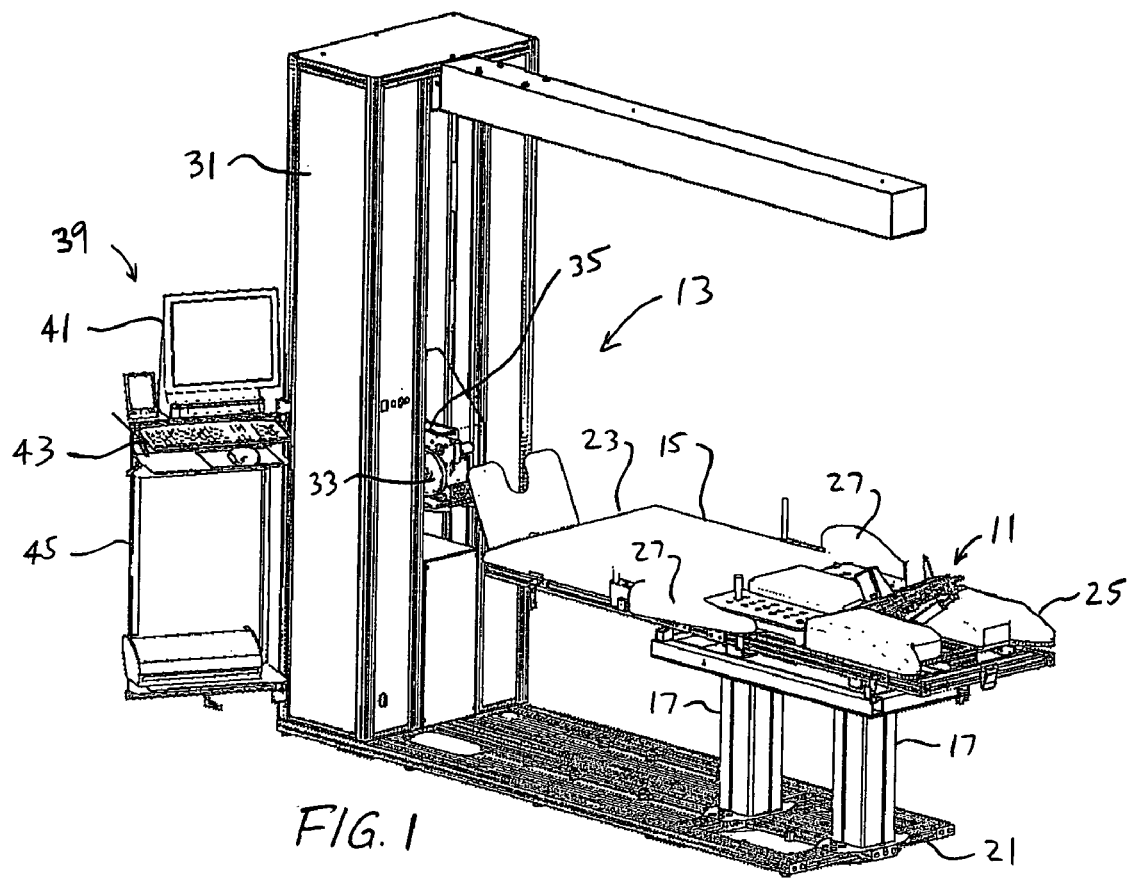
FIG. 1 illustrates a perspective view of a vertebral distraction apparatus having a cervical traction device according to the present invention mounted thereon.
Figure 2:
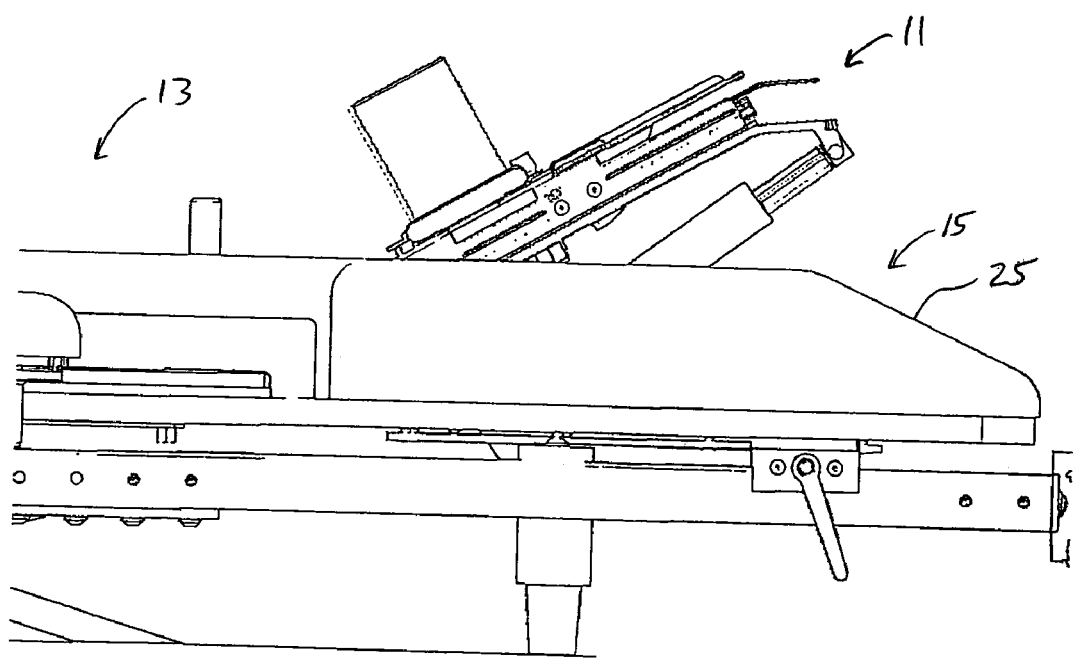
FIG. 2 depicts a partial side view of the vertebral distraction apparatus of FIG. 1.

In the following detailed description of the preferred embodiments, reference is made to the accompanying drawings, which form a part hereof, and in which is shown by way of illustration specific preferred embodiments in which the invention may be practiced. These embodiments are described in sufficient detail to enable those skilled in the art to practice the invention, and it is understood that other embodiments may be utilized and that logical software, electrical, mechanical, structural, and material changes may be made without departing from the spirit or scope of the invention. To avoid detail not necessary to enable those skilled in the art to practice the invention, the description may omit certain information known to those skilled in the art. The following detailed description is, therefore, not to be taken in a limiting sense, and the scope of the present invention is defined only by the appended claims.

Referring to FIG. 1–4, a cervical traction device 11 according to the present invention is mounted on a conventional vertebral distraction apparatus 13. As referred to herein, the vertebral distraction apparatus 13 should be understood to include any apparatus that typically would be used to apply forces to vertebra in a person's back, including but not limited to vertebral traction machines and vertebral decompression machines. The vertebral distraction apparatus 13 illustrated in FIGS. 1–4 includes a bed 15 mounted on a plurality of support posts 17, which may be telescopic to allow height adjustment of the bed relative to a floor 19. The support posts 17 terminate at a base plate 21, which further stabilizes the bed 15. Bed 15 includes a first end 23, or foot end, and a second end 25, or head end. When a patient is placed on the bed 15, the feet of the patient are typically oriented toward the first end 23 of the bed, and the head of the patient is typically oriented toward the second end 25 of the bed 15. The bed 15 further includes a pair of armrests 27 for supporting the patient's arms during treatment.

Figure 3:
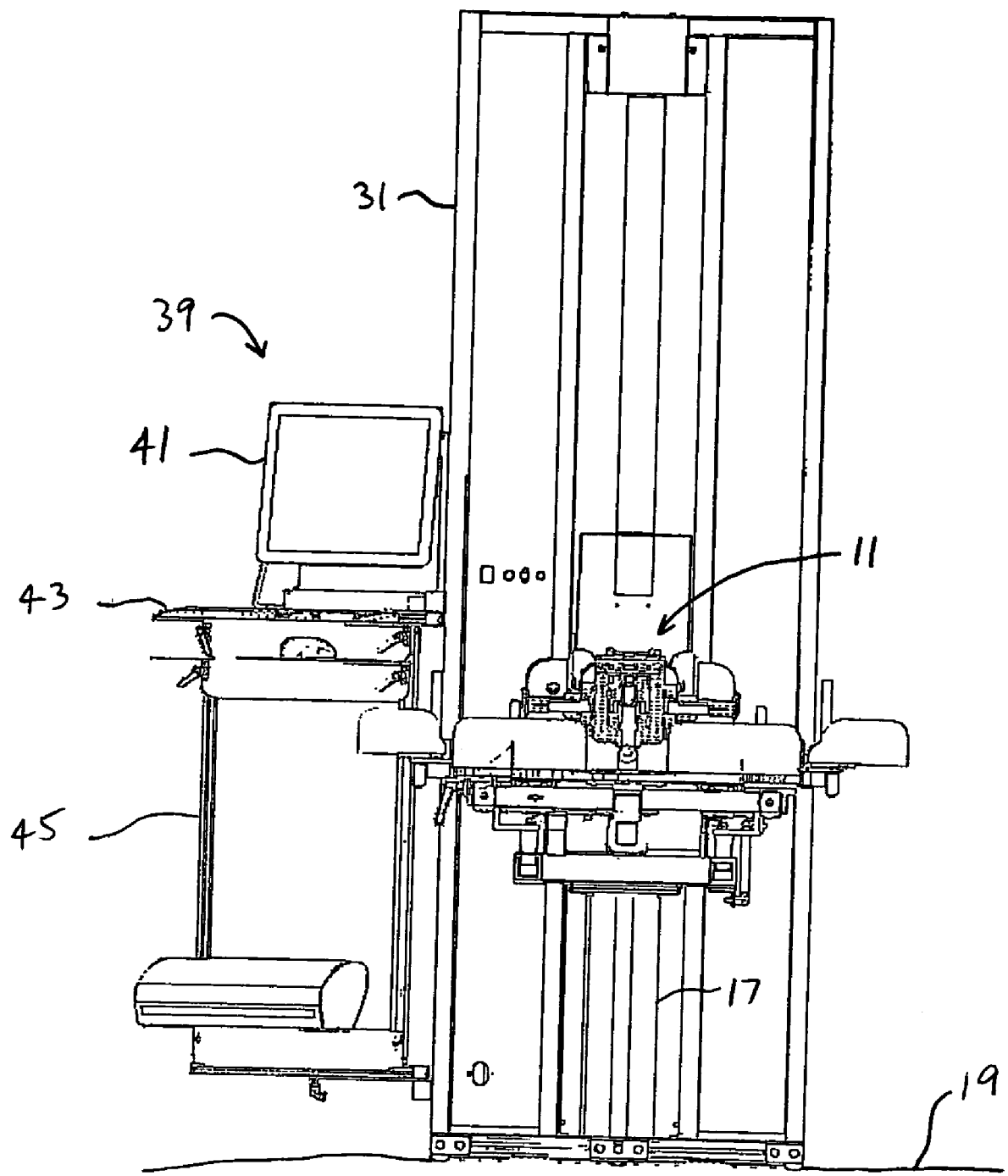
FIG. 3 illustrates a front view of the vertebral distraction apparatus of FIG. 1.
Figure 4:
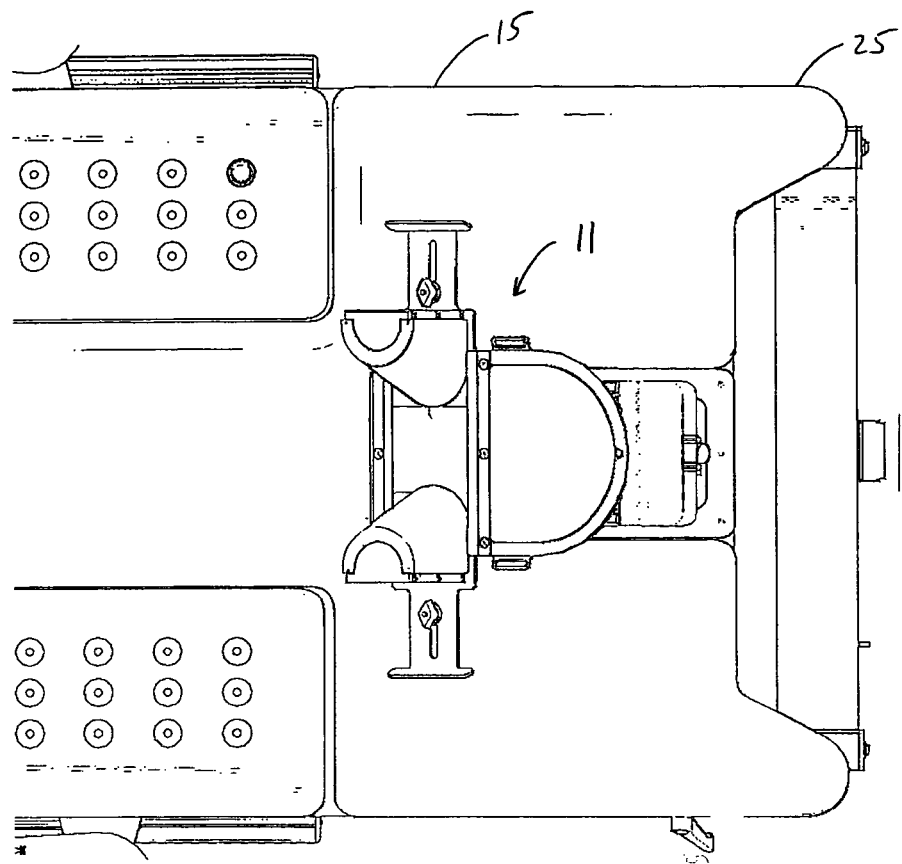
FIG. 4 depicts a partial top view of the vertebral distraction apparatus of FIG. 1.

At the first end 23 of bed 15, a pedestal 31, or distraction head, is disposed. The bed 15 may be adjustably attached to the pedestal 31 or may be independently positioned relative to the pedestal 31. Pedestal 31 houses the equipment necessary for applying distraction forces (either traction or decompression forces) to the vertebra in a person's back. In most instances, pedestal 31 includes a winch 33 having a clutch-operated motor 35. The winch 33 is connected to a harness, strap, rope, or other flexible line (not shown) that can be positioned around the legs or waist of the patient lying on the bed 15. Through the application of force applied by the clutch-operated motor, distraction of the patient's vertebra, especially the lower vertebra, is accomplished. Pedestal 31 may also include a computing system 39 having a monitor 41, an input panel 43, or keyboard, a processor (not shown), and memory (not shown). The computing system 39 is used to monitor and/or control the application of force during the distraction of the lower vertebra and may also store historical data about the particular patient being treated. As best illustrated in FIG. 3, a computer rack 45 may be adjustably connected to the pedestal 31 for supporting the monitor 41. The adjustable connection of the computer rack 45 to the pedestal 31 allows the height of the computer rack 45 to be adjusted to provide easy access by a therapist treating the patient.

The pedestal 31 is typically located near the foot end 23 of the bed 15 so that the motor 35 housed within the pedestal 31 for applying the lower vertebral distraction force is located in close proximity to the lower vertebra. The pedestal 31 could alternatively be located near the head end 25 of the bed 15. This positioning of the pedestal 31 would require a system of pulleys to route a strap from the head end 25 of the bed 15 to the foot end 23 of the bed to enable application of the distraction forces from the foot end 23 of the bed 15. Alternatively, lower vertebral distraction forces could potentially be applied from the head end 25 of the bed 15 if a harness was connected to the shoulders, arms, or upper body of the patient.

Figure 5:
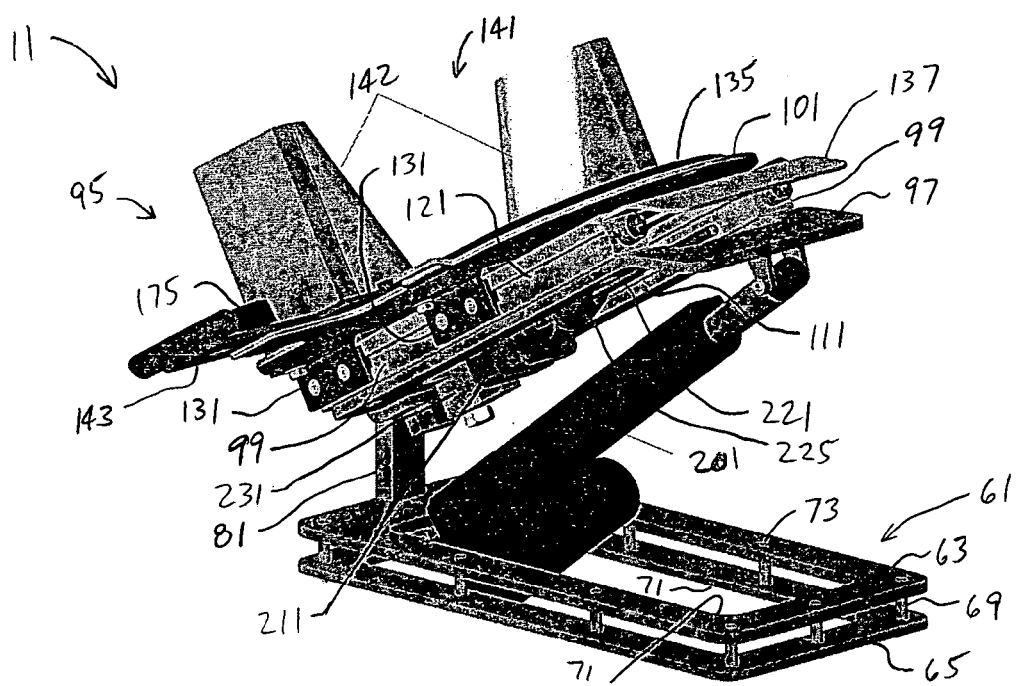
FIG. 5 illustrates a first perspective view of the cervical traction device of FIG. 1.
Figure 5A:
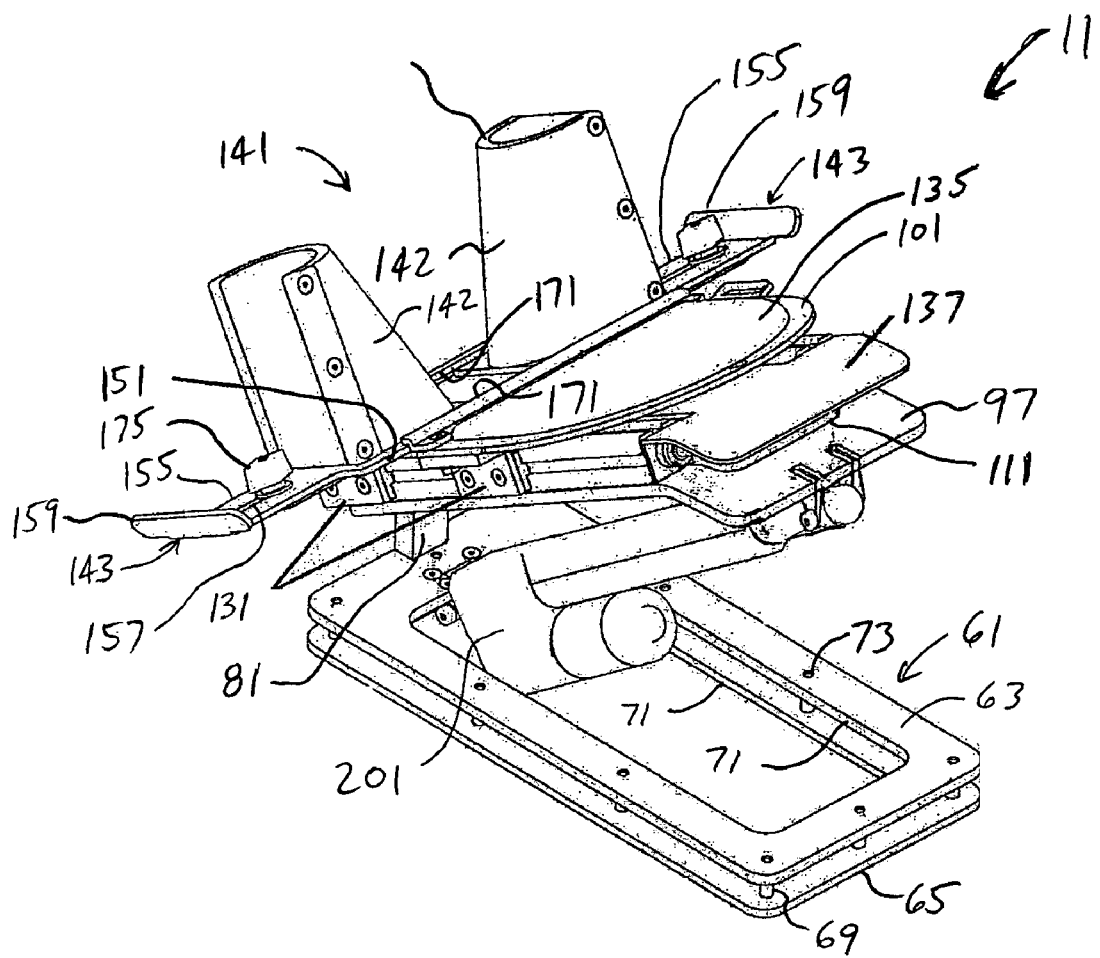
FIG. 5A depicts a second perspective view of the cervical traction device of FIG. 1.
Figure 6:
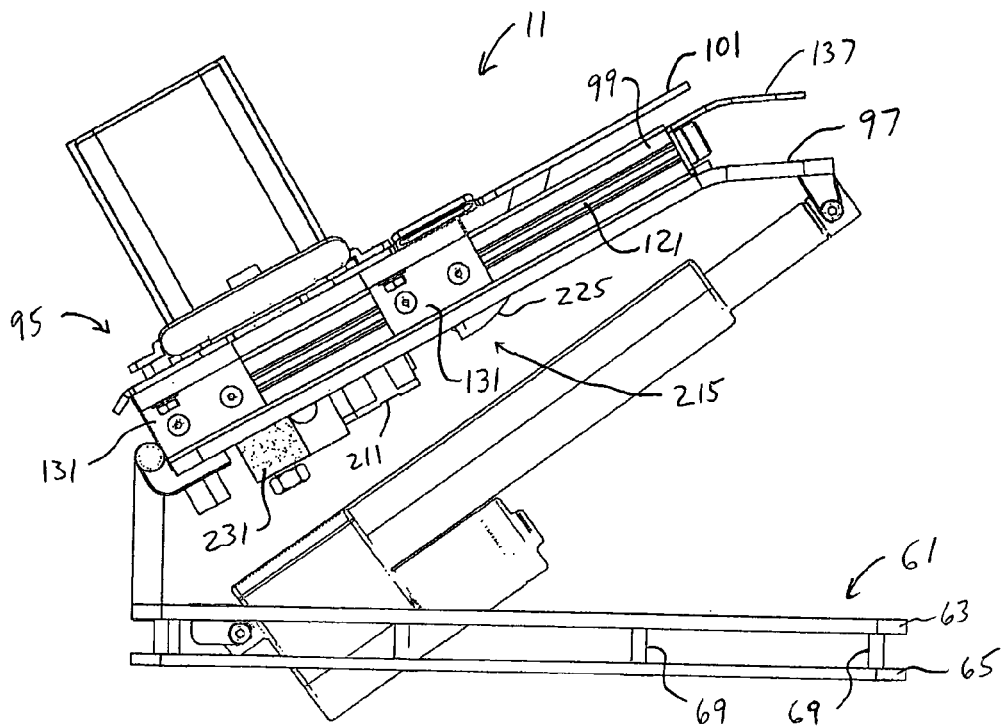
FIG. 6 illustrates a side view of the cervical traction device of FIG. 1 shown in an elevated position.
Figure 7:
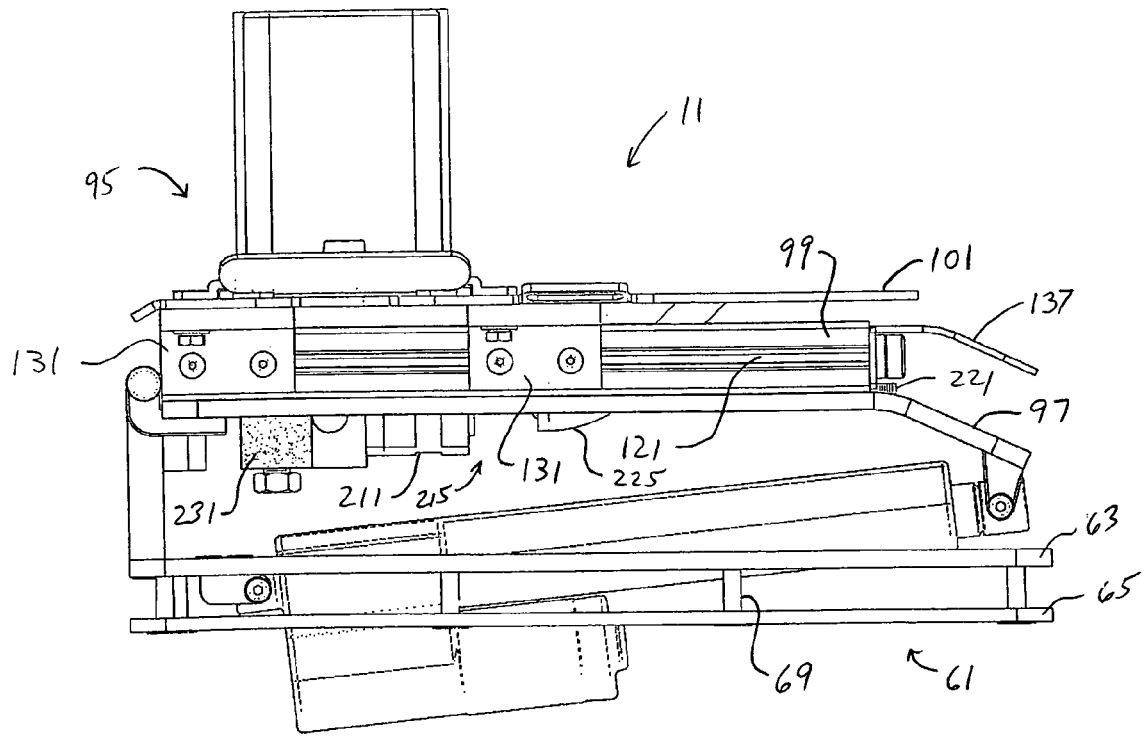
FIG. 7 depicts a side view of the cervical traction device of FIG. 1 shown in a non-elevated position.

Referring to FIGS. 5–7, the cervical traction device 11 according to the present invention is illustrated independently of the bed 15 in more detail. The cervical traction device 11 generally includes a base 61 having an upper base plate 63 and a lower base plate 65 connected in spaced opposition to one another by a plurality of spacers 69. Each of the base plates 63, 65 includes a center aperture 71, and the spacers 69 are arranged outside of the central apertures 71 near the perimeter of each base plate 63, 65. Preferably, mounting holes 73 pass through each of the base plates 63, 65 and the spacers 69 for mounting the base 61 to the bed 15 or another stabilizing object. Base 61 further includes a stabilization post 81 connected at one end to the upper base plate 63.

An elevation assembly 95 includes an elevation support plate 97, a pair of track members 99, and a cranial support plate 101 and is pivotally connected to the stabilization post 81. Each component of the elevation assembly 95 is meant to be angularly adjustable (or elevated) relative to the base 61, therefore any of these components could be pivotally connected to the stabilization post 81. However, in a preferred embodiment, the elevation support plate 97 is pivotally connected to the stabilization post 81. The elevation support plate 97 includes a central aperture 111, and each of the track members 99 is rigidly connected to an upper surface of the elevation support plate 97 outside of the central aperture 111 in spaced opposition to the other track member 99. Preferably, the track members 99 are extruded from a durable metal material such as steel and include a receiving channel 121. The track members 99 are mounted substantially parallel to one another such that the receiving channels 121 face outward. It is possible, however, to have receiving channels on both sides of the track members 99, or alternatively, to have only one receiving channel 121 per track member 99 and orient the receiving channels 121 inward. The receiving channels 121 are provided to receive bearings and therefore, positioning of the receiving channels 121 (and bearings) farther apart will provide better overall support.

Cranial support plate 101 is slidingly attached to the track members 99 through the use of self-aligning bearings 131. Preferably, four bearing units 131 are rigidly attached to the cranial support plate 101, and the receiving channel 121 on each track member 99 slidingly receives two of the bearing units. The bearings permit movement of the cranial support plate 101 relative to the elevation support plate along an axis parallel to the receiving channels 121. Cranial support plate 101 preferably includes a cushioned head pad 135 for making a patient being treated by the cervical traction device 11 more comfortable. During treatment, the back of the patient's head rests on the head pad 135. A hair guard 137 is rigidly attached to the track members 99 and assists in preventing the patient's hair from becoming entangled in the moving parts of the cervical traction device 11.

The cervical traction device includes a cervical force application member 141 for applying a cervical distraction force to a person's cervical vertebra. In general, the term "cervical force application member" used to refer to any of the components that are driven in order to apply the cervical distraction force. In a preferred embodiment, the cervical force application member 141 includes the cranial support plate 101 and a pair of occiput posts 142. Occiput posts 142 are rigidly connected to a pair of occiput positioning plates 143. Each occiput post 142 includes a hemispherical wall 145. The walls 145 of the occiput posts are angularly canted to form a V-shape when the two posts are installed adjacent to one another. The occiput positioning plate 143 is connected to the wall 145 such that a flange 151 extends past the wall on both sides of the occiput post 142. Each occiput positioning plate 143 includes an adjustment region 155 having a slot 157 and a handle region 159. The flanges 151 of the occiput positioning plate 143 are slidingly received by positioning channels 171 on the cranial support plate 101. A thumbscrew 175 is placed through slot 157 and a corresponding slot (not shown) in the cranial support plate 101. By selectively loosening or tightening the thumbscrew 175, each occiput post 142 can be independently adjusted on the cranial support plate 101 in a lateral direction. This allows the distance between the occiput posts 142 to be varied for individual patients.

The occiput posts 142 are the preferred method of applying force to the cervical vertebra of a patient. The occiput posts 142 are configured to be placed around the patient's neck just beneath the occipital portion of the skull. As force is applied to the occiput posts 142, the force is gently transferred to the head of the patient, thereby minimizing the discomfort that is sometimes associated with cervical distraction. Although the occiput posts 142 are preferred, it should be apparent to a person of ordinary skill in the art that other cervical force application members 141 could be used instead. For example, a pair of lateral support bars could be positioned at the base of the patient's skull and across the patient's chin to apply cervical distraction forces. Alternatively, a harness system could be attached to the cranial support plate 101 for supplying the needed force to the patient's head. Another example could be to have a molded cavity integrally formed on the cranial support plate 101 for surrounding at least a portion of the patient's head.

A linear actuator 201 is pivotally connected at one end to the upper base plate 63 and is pivotally connected at a second end to the elevation support plate 97. The linear actuator is positioned within the central apertures 71 of the base plates 63, 65 so that it can operate without obstruction. The linear actuator 201 provides selective positioning of the elevation assembly 95 (the elevation support plate 97, the track members 99, the cranial support plate 101, and the occiput posts 142) either prior to or during treatment of a patient so that the application of force can be properly concentrated on particular areas of the cervical vertebra. The linear actuator 201 can be adjusted between a fully elevated position (shown in FIG. 6) and a non-elevated position (shown in FIG. 7). Preferably, the non-elevated position would allow the patient's neck to be substantially parallel with the bed 15 at an angle of zero (0) degrees. The fully elevated position preferably positions the patient's neck at an angle of thirty (30) degrees from the surface of the bed 15. Of course, the linear actuator 201 is capable of positioning the elevation assembly 95 at any angle between the non-elevated and fully elevated positions. It is also important to note that while the maximum angle is preferred to be thirty (30) degrees, this design parameter could be increased or decreased. Finally, while it is preferable to use a linear actuator for adjusting the elevation of the cervical traction device 11, the elevation of the device could be positioned manually.

A motor 211 is positioned within the central aperture 111 of the elevation support plate 97 and is rigidly connected to either the elevation support plate 97 or the track members 99. A direct drive system 215 is operably connected between the motor 211 and the cranial support plate 101. For the purposes of the present invention, the phrase "direct drive system" includes any direct, non-flexible linkage between a driving element (e.g. a motor) and a driven element (e.g. cranial support plate 101) that allows a transfer of power between the two elements. Direct drive systems do not include flexible power transfer linkages such as cables, ropes, straps, webbing, or other materials that are typically used with winches and pulleys. The direct drive system 215 according to the present invention preferably includes a threaded shaft 221 rotatably connected to the motor 211. The shaft 221 includes a plurality of threads on its outer surface for threadingly receiving a screw transfer member 225. Screw transfer member 225 is rigidly connected to a lower surface of the cranial support plate 101. As motor 211 turns, shaft 221 turns in response, thereby driving screw transfer member 225 along the shaft 221 in a direction determined by the direction the motor 211 turns. The cranial support plate 101 follows the movement of screw transfer member 225. The motor 211 is therefore capable of applying a force to the cranial support plate 101 and driving the cranial support plate 101 in either of two directions.

Motor 211 is preferably a stepper motor. A stepper motor allows very fine, incremental control over the force applied to the cranial support plate 101 and the resulting movement by the cranial support plate 101. The stepper motor provides controlled application of force in both directions in very small increments. The stepper motor is preferably sized to provide up to fifty (50) pounds of force and provides this force by moving the screw transfer member 225 one hundred and twenty five thousandths (0.0125) of an inch for each step of the motor. Even finer control is provided by using control software, which allows incremental advancement of up to 0.0125/4 inches. In addition to the control advantages provided by the stepper motor, the stepper motor also provides desirable characteristics if power is lost or interrupted during the treatment of a patient. Because of the configuration of the magnets within a stepper motor, a loss of power to the motor does not immediately release all force being applied by the motor. Instead, the force being applied by the motor is relieved slowly in the event of a power loss. This is an important advantage since an instantaneous release of tension from the neck of a patient being treated could cause discomfort and injury. Although the stepper motor is sized to provide up to fifty (50) pounds of force, during most cervical treatments, the force applied by the motor will not exceed 30–40 pounds.

Other types of motors could be used in place of the stepper motor; however, it is desired to maintain good control over the application of force to the cranial support plate 101. An example of another motor type that would satisfy this function includes a servo motor.

A strain gauge 231 is operably connected to the motor 211 to measure the application of force applied by the motor to the cranial support plate 101. Strain gauge 231 is preferably electrically connected to a control system that is discussed in more detail below.

Figure 8:
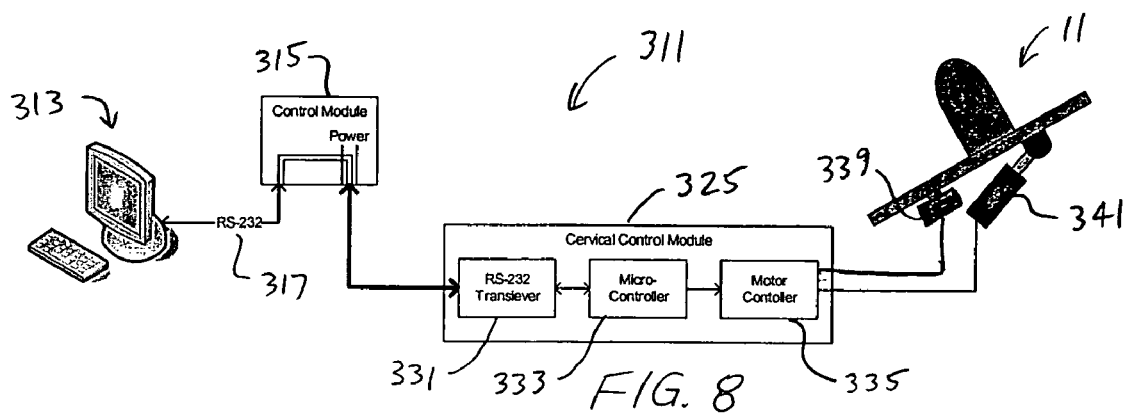
FIG. 8 illustrates a schematic of the electrical and mechanical connections associated with the cervical traction device of FIG. 1.

FIG. 8 illustrates a block diagram of an exemplary electrical system 311 for controlling the cervical traction device 11 during treatment of a patient. As shown, a computing system 313 is electrically coupled to a control module 315 via communications bus 317. In one embodiment, the computing system 313 is a conventional personal computer executing a software program with a graphical user interface (GUI) for enabling an operator to establish and/or modify a treatment profile for individual patients. Alternatively, the computing system 313 is an integrated unit having a user interface formed of keypads and an optional display, such as a liquid crystal display, to display the patient treatment profile. When cervical traction device 11 is used with a conventional vertebral distraction machine, computing system 313 will likely be located near pedestal 31 similar to computing system 39 (see FIG. 3). The control module 315 may be located with or separate from the computing system 313. The control module 315 may include a processor (not shown) and transceiver (not shown) for communicating with the computing system 313. The control module 315 is operable to communicate with the computing system 313 for receiving patient profile control commands from the computing system 313. The control module may process the patient profile control commands for communication to a cervical control module 325. The cervical control module 325 may be located at the computing system 313, between the computing system 313 and the cervical traction device 11 (e.g., below the bed 15 of FIG. 1), or at the cervical traction device 11. The communications link between the computing system 313 and cervical control module 325 may be wired or wireless.

The cervical control module 325 may include a communication transceiver 331, micro-controller 333, and motor controller 335. The transceiver 331 may communicate via an RS-232 or other protocol as understood in the art for communicating data in a digital or analog format. The micro-controller 333 may be any micro-controller as understood in the art capable of performing mathematical and logical operations. Alternatively, the micro-controller may be a programmable unit and/or logic circuit that is capable of performing mathematical and logical operations. The micro-controller 333 is operable to execute software or firmware that controls the electro-mechanical operations of the cervical traction device 11 by generating commands and operating in conjunction with the motor controller 335 to control one or more electro-mechanical components 339 and 341 at the cervical traction device 11.

The electro-mechanical components 339 and 341 of the cervical traction device 11 may be a stepper motor and a linear actuator, respectively. The stepper motor may be utilized to apply a force to the head of the patient (similar to motor 211) while the linear actuator may be utilized to adjust the angle of the cervical traction device 11 (similar to linear actuator 201). Although two electro-mechanical components are shown, it should be understood that one or more electro-mechanical components may be utilized to control mechanical operation of the cervical traction device 11 for treating a patient in accordance with the principles of the present invention. As depicted, control of the electro-mechanical components 339 and 341 of the cervical distraction device is performed by communicating one or more signals to the cervical distraction device 11. Again, the signals may be digital or analog as opposed to a mechanical or other force for moving mechanical components at the cervical distraction device 11.

The micro-controller 333 further may be utilized to receive a feedback signal from one or more sensors (such as strain gauge 231 illustrated in FIG. 6) coupled to the cervical distraction device 11. The sensors may be position, speed, strain, and/or acceleration sensors and utilized for enabling the motor-controller 335 to accurately position and move the cervical distraction device 11 in following the patient treatment profile commands generated by the computing system 313. Depending on the feedback provided by the sensors, the micro-controller 333 may also include kill switch functionality to direct the motor-controller 335 to shut down the motor. The kill switch would be activated if sensor values exceed predefined parameters.

Figure 9:
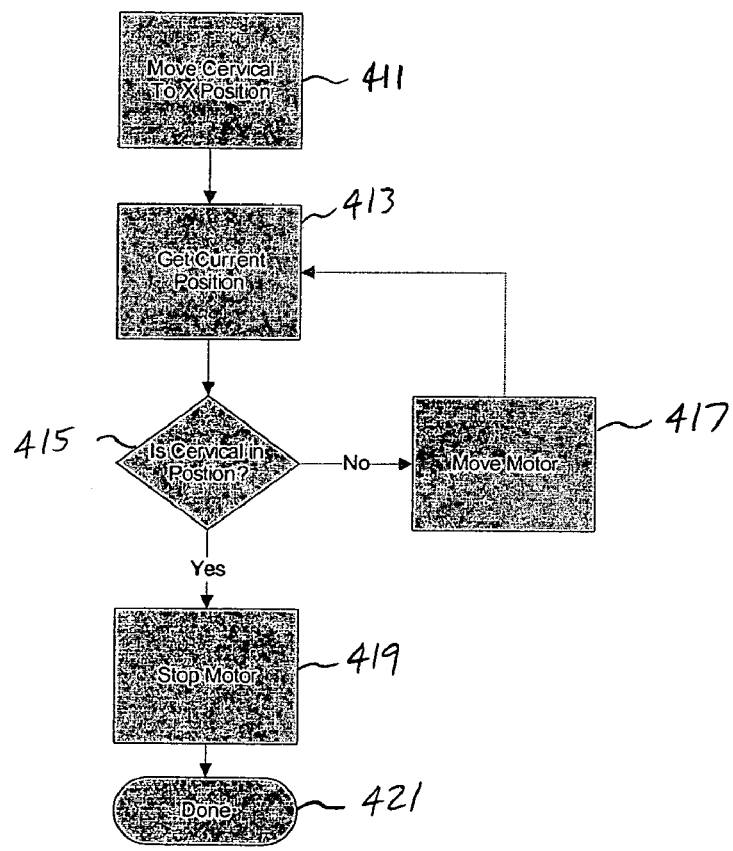
FIG. 9 depicts a flow chart showing the steps involved in positioning the cervical traction device of FIG. 1.

In controlling the electro-mechanical components of the cervical distraction device 11, FIG. 9 is a flow diagram describing basic control thereof. The control process starts at step 411. At step 411, the cervical force application member is moved to a first position. At step 413, the actual position is sensed and fed back to determine the actual current position. A determination is made at step 415 if the cervical force application member is at the commanded position. If not, then a correction signal is sent at step 417 to alter the position of the cervical force application member via an electro-mechanical component. Steps 413–417 are repeated until the position is correct. Once the position is correct, the motor is stopped at step 419. The control process ends at step 421.

Figure 10:
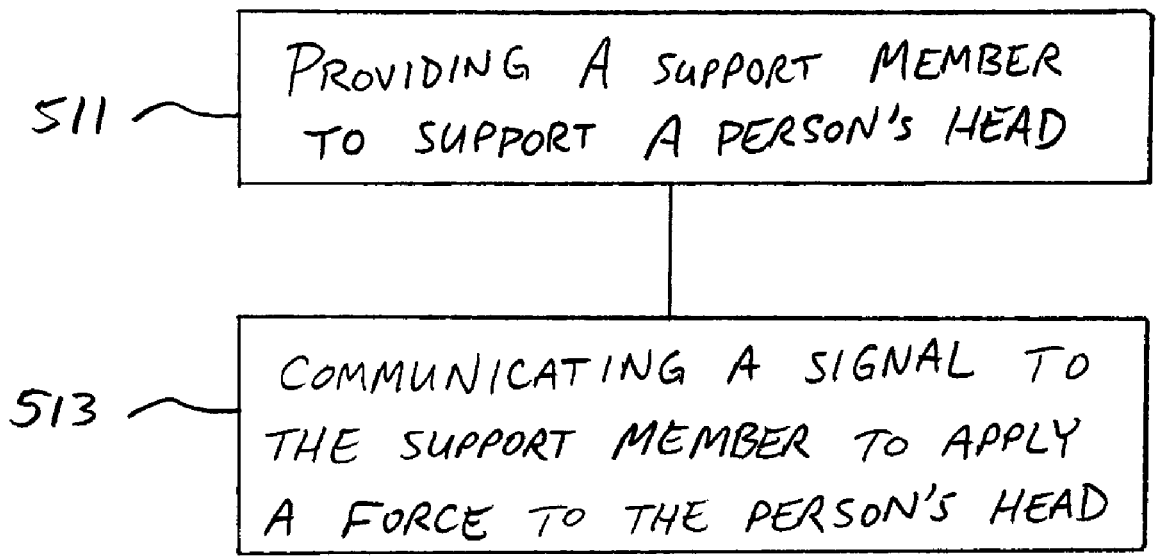
FIG. 10 illustrates a flowchart showing a method of decompressing cervical vertebra according to the present invention.

FIG. 10 illustrates a method for distracting a cervical vertebra according to the present invention. The method includes the steps of providing a support member to support a person's head at step 511 and communicating a signal to the support member to apply a force to the person's head at step 513. The communicated signal is preferably delivered to a stepper motor at the support device, which drives the support device through a direct drive system. The force applied to the person's head may be monitored, and is capable of being gradually decreased.

The cervical traction device of the present invention presents many advantages over existing equipment used to distract or decompress cervical vertebra. One advantage of the cervical traction device is that it provides far more control over the traction or decompression process by providing a direct drive system between the driving component (i.e. a motor) and the driven component (i.e. a cervical force application member). The direct drive system eliminates the need for flexible power transfer devices that are typically used with winches and motors mounted remotely from the patient's head. By mounting the motor for applying the cervical distraction force more closely to the patient's head where the force is to be applied, and by applying the force through the direct drive system, almost no flexibility is introduced between the motor and the person's head, thereby providing a very controlled and efficient application of force.

When mounted on a vertebral distraction apparatus, the motor linked to the cervical traction device is completely separate from the motor traditionally used with the vertebral distraction apparatus to provide lower vertebral distraction forces. As mentioned above, the inclusion of this additional motor allows much more control over the forces applied to the cervical vertebra. The force control of the cervical traction device is further enhanced by the use of a stepper motor sized specifically for providing cervical distraction forces. The inherent design of a stepper motor allows the gradual and controlled application of force. Since the stepper motor is dedicated to the cervical traction device, it can be much smaller than the traditional motor used to apply lower vertebral distraction forces. Finally, utilizing a stepper motor in the distraction system design allows the application of force to be gradually disengaged in the event of a power interruption to the motor.

Although many of the examples discussed herein are applications of the present invention with conventional vertebral distraction machines, the cervical traction device can be used independently of such machines or can be integrated into new vertebral distraction machines. It should further be appreciated that the materials used to construct the cervical distraction device could vary, but preferably include materials having sufficient strength to adequately transmit distraction forces to a patient's cervical vertebra. It should further be appreciated that certain movable components of the cervical traction device, such as the occiput posts, can be manually adjusted as explained herein, or could be automatically adjusted using motors and sensors. Finally, it should be appreciated that the control, application, and monitoring of force by the cervical traction device may be controlled by a software program associated with the computing system previously discussed. This program may provide simple control of the cervical traction device, thereby enabling a therapist to "dial in" a particular force, or may include a plurality of pre-established or custom routines that apply varying forces over varying time periods to the patient.

It should be apparent from the foregoing that an invention having significant advantages has been provided. While the invention is shown in only a few of its forms, it is not just limited but is susceptible to various changes and modifications without departing from the spirit thereof.

We claim:

1. A cervical traction device comprising:
   a base;
   an elevation support plate pivotally connected to the base;
   at least one track member rigidly connected to the elevation support plate;
   a cervical force application member slidingly connected to the at least one track member;
   an actuator pivotally connected to the base and the elevation support plate;
   a stepper motor rigidly connected to one of the elevation support plate and the at least one track member;
   a threaded shaft operably connected to the stepper motor and rotatably responsive to output by the stepper motor;
   a screw transfer member threadingly received on the threaded shaft and rigidly connected to the cervical force application member;
   wherein the actuator selectively positions the elevation support plate between a non-inclined position and an inclined position; and
   wherein rotation of the threaded shaft by the stepper motor drives the screw transfer member, thereby moving the cervical force application member relative to the base.

2. A cervical traction device according to claim 1, wherein the cervical force application member includes a pair of occiput posts.

3. A cervical traction device according to claim 1, wherein the cervical force application member includes a harness.

4. A cervical traction device according to claim 1, wherein the at least one track member includes a pair of track members.

5. A cervical traction device according to claim 1 further comprising a hair guard disposed below the cervical force application member.

6. A cervical traction device according to claim 1, wherein the cervical force application member further comprises:
   a cranial support plate;
   a pair of occiput posts adjustably mounted to the cranial support plate; and
   a bearing connected to the cranial support plate for slidingly mounting the cranial support plate to the at least one track member.

7. A cervical traction device according to claim 6, wherein the at least one track member includes a pair of track members.

8. A cervical traction device according to claim 1, wherein the actuator is capable of elevating the elevation support plate at an angle between 0 and 30 degrees relative to the base.

* * * * *